United States Patent [19]

de lis Masilungan

[11] 4,096,271
[45] Jun. 20, 1978

[54] SLOW RELEASE INJECTABLE FORMULATIONS OF TETRAMISOLE AND DERIVATIVES IN BENZYL BENZOATE

[75] Inventor: Fleur de lis Masilungan, Trenton, N.J.

[73] Assignee: American Cyanamid Company, Stamford, Conn.

[21] Appl. No.: 821,258

[22] Filed: Aug. 3, 1977

[51] Int. Cl.$^2$ .................... A61K 31/425; A61K 47/00
[52] U.S. Cl. ..................................... 424/270; 424/358
[58] Field of Search ............................... 424/270, 358

[56] References Cited
PUBLICATIONS

Pryor et al. — Chem. Abst., vol. 74, (1971), p. 91194h.

*Primary Examiner*—Sam Rosen
*Attorney, Agent, or Firm*—H. G. Jackson

[57] ABSTRACT

The invention relates to novel slow release injectable formulations of tetramisole and certain derivatives thereof in benzyl benzoate. These formulations are markedly safer, less toxic, and cause milder side effects when administered in larger than the recommended dosages to homothermic farm and companion animals, as compared to conventional aqueous buffered injectable formulations containing pharmaceutically acceptable salts of the same compounds. The invention also relates to the use of the slow release injectable formulations for the control of helminths infecting homothermic farm and companion animals.

20 Claims, No Drawings

SLOW RELEASE INJECTABLE FORMULATIONS OF TETRAMISOLE AND DERIVATIVES IN BENZYL BENZOATE

Compounds of formula (I)

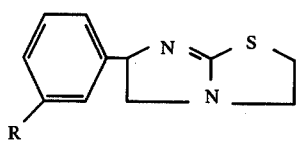

wherein R is hydrogen, amino, i-butyrylamino, trimethylacetylamino or benzoylamino; and the compounds are the racemic mixtures and the optically active isomers thereof are highly effective for the control of helminths infecting homothermic farm and companion animals such as sheep, goats, horses and swine, and dogs and cats. The anthelmintics may be administered to the animals in, or with their feed or drinking water; or may be administered orally in the form of pills, boluses, tablets and the like. The formula (I) anthelmintics may also be formulated as drenches, pour-ons, implants and injectables.

Injectable formulations are one of the preferred modes of administration, since they allow the introduction and delivery of the above anthelmintics into the circulatory system of the animal via subcutaneous and/or intramuscular injections in precisely calculated dosages. Propylene glycol is a commonly used solvent for such formulations. Unfortunately, the compounds of formula (I) and their salts are quite toxic to certain farm and domestic animals such as swine, dogs and cats, and the margin of safety between the maximum effective and minimum toxic dose in the homothermic farm and companion animals is small. Thus an accidentally administered overdose could poison, and might even kill the animal it was supposed to protect. Slow-release injectable formulations of formula (I) compounds possessing a wider margin of safety in homothermic farm and companion animals are highly desirable.

Pharmaceutically acceptable salts of formula (I) compounds administered as conventional aqueous buffered subcutaneous (and/or intramuscular) injections to homothermic farm and companion animals are rapidly absorbed from the site of the injection, and will reach the circulatory system of the animals in a relatively short period of time. Anthelmintically effective amounts of the above formula (I) compounds will appear in the animals circulatory system, if the formula (I) compounds are administered at or below the recommended maximum dosage of about 8 mg levamisole hydrochloride equivalent/kg body weight for farm animals and about 4 mg levamisole hydrochloride equivalent/kg for companion animals. The level thus attained is maintained only for a relatively short period of time, and then the active compound is rapidly eliminated from the animals circulatory system.

As stated above, it would be advantageous and highly desirable to find slow release injectable formulations of formula (I) compounds, which would possess a wider margin of safety in homothermic farm and companion animals, and thus would make possible, if desired, the administration of larger than the hitherto recommended maximum dosages of 4 to 8 mg levamisole hydrochloride equivalent/kg body weight to the animals.

I have found that injectable formulations comprising an anthelmintic compound represented by formula (I)

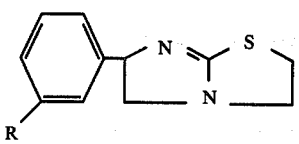

wherein R is hydrogen, amino, i-butyrylamino, trimethylacetylamino or benzoylamino; and the compounds which are the racemic mixtures and the optical isomers thereof dissolved in benzyl benzoate, are slow release anthelmintic injectable formulations when administered subcutaneously (or intramuscularly) to homothermic farm and companion animals. Additionally, overdosages up to five times the recommended maximum level are well-tolerated by the recipient animals, with only transient, short lived, toxic symptoms accompanying such overdosages.

It is essential, that the benzyl benzoate utilized in the formulations be free of hydrohalo acids (e.g. hydrochloric acid) and/or halogen containing organic compounds (e.g. benzylchloride), which in the presence of, or when brought in contact with, water would react with same to form the hydrohalo acids. The presence of the hydrohalo acids in the formulation would be detrimental since the formula (I) bases would be rapidly precipitated from their solutions as the corresponding salts.

The most preferred compound of the group represented by formula (I) is dl-6-phenyl-2,3,5,6-tetrahydroimidazo[1,2-b]-thiazole (tetramisole) and especially its l isomer, also known as levamisole. Among the optically active isomers of formula (I) compounds, the l isomers are generally preferred since they appear to be biologically more active than are the corresponding d isomers.

Conventional aqueous buffered injectable formulations utilize water soluble salts of formula (I) anthelmintics, prepared from the corresponding formula (I) bases and a pharmaceutically acceptable acid. These salts will migrate rapidly from the site of the injection into the animals circulatory system. Thus, an accidentally administered overdose may rapidly reach a toxic and possibly lethal drug level in the recipient animals circulatory system. An additional disadvantage of the aqueous injectables is the relative instability of the above-referred-to salts of formula (I) compounds in these solutions.

Advantageously, we now find that the migration of formula (I) bases from the site of the injection is in general, much slower than that of their corresponding salts. Consequently, when administered to homothermic farm and companion animals, even in larger than the recommended dosages, these compounds will reach in the animals circulatory system an anthelmintically effective level and will maintain the anthelmintically effective level for a prolonged period of time with only mild toxic symptoms from which the recipient animals rapidly recover.

The slow release injectable formulations of the invention comprising the solution of a compound of formula (I)

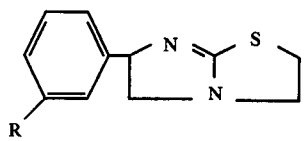

(I)

wherein R is hydrogen, amino, i-butylrylamino, trimethylacetylamino or benzoylamino and the racemic mixtures and the optical isomers thereof in benzyl benzoate in amounts corresponding to 5% to 20% w/v levamisole hydrochloride equivalent, and preferably 6% to 18.2% w/v levamisole hydrochloride equivalent are inherently safer than conventional aqueous formulations and are well tolerated even when administered at the rate of five times the recommended maximum dosage, and the storage stability of the sterilized injectables is improved.

In the examples below levamisole hydrochloride is used as a standard. Free base equivalents of the compounds of this invention are reported in the table below:

| R | Free Base Equivalents (in mg) of 1 mg levamisole · HCl |
|---|---|
| H | 0.8486 |
| amino | 0.9109 |
| i-butyrylamino | 1.2020 |
| trimethylacetylamino | 1.2603 |
| benzoylamino | 1.3433 |

The most preferred slow-release formulation comprises a solution of levamisole, 1-6-phenyl-2,3,5,6-tetrahydroimidazo[2,1-b]thiazole in benzyl benzoate containing the compound in amounts equivalent to 6% to 18.2 % levamisole hydrochloride.

For the control of helminths infecting homothermic farm and companion animals such as sheep, goats, horses and swine, and dogs and cats, the above novel slow-release formulations are administered to the animals as one or more subcutaneous (or intramuscular) injection(s), designed to deliver 5 mg to 40 mg and preferably 6 mg to 16 mg levamisole hydrochloride equivalent/kg body weight.

The following non-limiting examples are provided to further illustrate the invention.

EXAMPLE 1

Evaluation of the safety of 18.2% levamisole aqueous injectable formulation in pigs at 8, 16, 24, 32, 48 and 64 mg/kg levamisole hydrochloride equivalent

| Composition of formulation | |
|---|---|
| Ingredients* | % |
| Levamisole . HCl equivalent as levamisole phosphate | 18.2 |
| Propyl paraben | 0.0205 |
| Methyl paraben | 0.162 |
| Sodium hydroxide | 0.047 |
| Sodium metabisulfite | 0.2 |
| Disodium edetate | 0.13 |
| Citric acid . H₂O | 3.47 |
| Sodium citrate . 2 H₂O | 2.08 |

-continued

| Composition of formulation | |
|---|---|
| Ingredients* | % |
| Distilled water q.s. ad | 100.00 |

*In grams except for water

Procedure

Thirty Yorkshire-Hampshire crossbred pigs are weighed, and are allocated to 6 groups of 5 pigs each. Water and swine grower ration are provided ad libitum (the composition of the swine grower ration is given at the end of this example).

At 4 days after weighing, each pig in groups A,B, C,D,E and F is injected subcutaneously in the right axillary space with the above injectable formulation at dosages of 8, 16, 24, 32, 48 and 64 mg levamisole hydrochloride equivalent/kg body weight.

The animals are under close observation on the day of medication and once daily for 7 days postinjection. Any toxic symptoms or mortality are recorded. The data obtained are summarized in Table I below.

Table I
Evaluation of the Safety of Regular Aqueous Buffered Levamisole Injectable Solution Containing the Equivalent of 18.2% w/v Levamisole Hydrochloride at 8, 16, 24, 32, 48 and 64 mg/kg body Weight Level, in Pigs

| | mg/kg Levamisole Hydrochloride Equivalent | Toxic Symptoms | Duration of Treatment Effects | Survivors per Total | Percent Mortality |
|---|---|---|---|---|---|
| A | 8 | none | — | 5/5 | 0 |
| B | 16 | T;F;E | 1 hour | 5/5 | 0 |
| C | 24 | T;F;E;A | 1 hour | 5/5 | 0 |
| D | 32 | S;T;E;L;D | 2.5 hours | 2/5 | 60 |
| E | 48 | S;T;E;L;D | 4 hours | 1/5 | 80 |
| F | 64 | E;L;D | | 0/5 | 100 |

A = Ataxia; D = Death; E = Emesis; F = Foamy muzzle; L = Lateral recumbency; S = Salivation; T = Tremors

| Composition of Swine Grower Ration | |
|---|---|
| Ingredients | % |
| Ground Corn | 78.00 |
| Soybean Oil Meal, 49% Protein | 17.50 |
| Fat, and Bone Meal, 50% Protein | 2.50 |
| Dicalcium Phosphate (18.5%P) | 0.75 |
| Iodized Salt | 0.50 |
| Limestone (38% Ca) | 0.60 |
| Mineral Premix[a] | 0.075 |
| Vitamin Premix[b] | 0.075 |
| | 100.00 | a) Minerals provided per ton of feed (ppm)
- Iron  75 ppm
- Copper  75 ppm
- Manganese  45 ppm
- Zinc  75 ppm b) Vitamins provided per ton of feed
- Vitamin A  3,000,000 I.U.
- Vitamin D  600,000 I.U.
- Riboflavin  6 g
- Pantothenic acid  15 g
- Niacin  30 g
- Vitamin $B_{12}$  15 mg
- Menadione  3 g
- Vitamin E  7,500 I.U.
- Choline  150 g

EXAMPLE 2

Evaluation of the safety of regular 9.1% levamisole injectable vs. an aqueous propylene glycol formulation containing 9.1% levamisole

| | Composition of the Formulations | |
|---|---|---|
| Ingredients* | Regular 9.1% | Aqueous Propylene Glycol 9.1% |
| Levamisole . HCl equivalent as levamisole phosphate | 9.1 | 9.1 |
| Propyl paraben | 0.0205 | 0.0205 |
| Methyl paraben | 0.162 | 0.162 |
| Sodium hydroxide 0.047 | 0.047 | |
| Sodium metabisulfite | 0.2 | 0.2 |
| Disodium edetate | 0.13 | 0.13 |
| Citric acid . H₂O | 3.47 | 3.47 |
| Sodium citrate . 2 H₂O | 2.08 | 2.08 |
| Propylene glycol | 0 | 50.0 |
| Dist. water q.s. ad | 100.0 | 100.0 |

*In grams, except for water

Preparation of the Formulations

The ingredients listed in the above table are dissolved in a portion of distilled water and the volume of the solution is then adjusted to 100 ml with distilled water, to yield formulations containing the equivalent of 9.1% w/v levamisole hydrochloride.

Procedure

Forty Yorkshire-Hampshire crossbred pigs, having an average weight of 65 lb, are used for the experiment. The pigs are separated in groups of 5 per pen. Water and Swine Grower Feed are provided ad libitum.

Individual pig weights are measured at 1 to 2 days before treatment for calculation of individual drug dosages.

| | Treatment Groups | | |
|---|---|---|---|
| Group | 9.1% w/v Formulation | Dosage* mg/kg | No. of Pigs per Group |
| A | Regular | 16 | 10 |
| B | aq. propylene glycol | 16 | 10 |
| C | Regular | 32 | 5 |
| D | aq. propylene glycol | 32 | 5 |
| E | Regular | 40 | 5 |
| F | aq. propylene glycol | 40 | 5 |

*Standard dosage is 8 mg/kg body weight

The experiment is conducted in two phases. In phase I, 5 male and 5 female pigs in group A are injected subcutaneously in the right axillary space with the regular 9.1% w/v levamisole injectable at 16 mg levamisole hydrochloride equivalent/kg body weight (2 times the recommended level).

Similarly, 5 male and 5 female pigs in group B are injected with the experimental 9.1% w/v levamisole in aqueous propylene glycol at 16 mg levamisole hydrochloride equivalent/kg body weight (2 times the recommended dosage). The animals are under close observation on the injection day and the following morning. Any symptoms of toxicity, mortality and onset and duration of the toxic symptoms are recorded.

Phase II is conducted 1 day after the phase I treatment. Pigs in groups C and D are injected subcutaneously with the regular 9.1% w/v levamisole injectable and the experimental 9.1% w/v levamisole in aqueous propylene glycol at 32 mg levamisole hydrochloride equivalent/kg body weight (4 times the recommended level). Pigs in groups E and F are injected subcutaneously with the respective formulations at 40 mg levamisole hydrochloride equivalent/kg body weight (5 times the recommended level). The animals are under close observation, and mortality and toxic symptoms are recorded. The data obtained are summarized in Table II below.

Table II

Evaluation of the safety of regular aqueous buffered levamisole injectable compared to a similar formulation containing propylene glycol; wherein both injectables contain 9.1% w/v levamisole hydrochloride equivalent, in pigs.

| Group | Formulation | mg/kg levamisole . HCl Equivalent | Clinical Observation | No. of Pigs Showing at least one of the Symptoms | Time became Normal (Hrs) | Survivors Per Total |
|---|---|---|---|---|---|---|
| A | Regular | 16 | T;F;V;l | 9/10 | 1-2 | 10/10 |
| B | aq. propylene glycol | 16 | T/F/V/L | 6/10 | 0.5-2 | 10/10 |
| C | Regular | 32 | T;F;S;A; C;R;L;D | 5/5 | 1-1.5 | 2/5 |
| D | aq. propylene glycol | 32 | T;F;S;A; C;R;L;D | 4/5 | 1-2 | 5/5 |
| E | Regular | 40 | T;A;F;C; R;D | 5/5 | | 0/5 |
| F | aq. propylene glycol | 40 | T;A;F;S; R;D | 5/5 | 2-2.5 | 2/5 |

A = Ataxia; D = Death; F = Foamy muzzle; C = Convulsions; L = Lethargy; R = Recumbency; T = Tremors; V = Vomiting: S = Salivation

EXAMPLE 3

The Safety of Levamisole Base-Benzyl Benzoate Injectable Formulation in Pigs

Formulation

Levamisole base is dissolved in benzyl benzoate (levamisole base 7.72 g real, benzyl benzoate q.s. ad 100 ml) to provide an injectable formulation containing the equivalent of 9.1% w/v levamisole hydrochloride.

Test animals

Twenty-four Yorkshire-Hampshire crossbred pigs (12 males and 12 females), having an average weight of 14.7 kg, are randomly distributed in 4 groups of 6 pigs each (3 males and 3 females). Water and a basal swine starter ration are offered ad libitum.

Procedure

Phase I

Individual pig weights are determined the same day of treatment for calculation of individual drug dosages. No more than 4 ml of injectable is placed subcutaneously at any injection site in the axillary region when administering the corresponding drug dosages. Pigs in group 1 serve as unmedicated controls, and receive 1 ml of normal saline per 11.34 kg body weight. Animals in groups 2, 3 and 4 are injected with the above formulations providing the equivalent of 8, 24 and 40 mg levamisole hydrochloride/kg body weight, respectively. Animals are observed after treatment continuously for 3 hours and at least once a day thereafter.

Phase II

The procedure is essentially the same as the one used in phase I. There is a 14 days interval between the beginning of this phase and phase I. The average weight of the pigs is 19.9 kg. The data obtained in phases I and II are summarized Table III below.

Table III

| | | Clinical observation and Symptoms | | No. of Pigs Showing at Least One of the Symptoms | | Survivors per Total | |
|---|---|---|---|---|---|---|---|
| Group* | mg/kg levamisole . HCl Equivalent | Phate I | Phase II | Phase I | Phase II | Phase I | Phase II |
| 1 | Unmedicated Controls | normal | normal | 0/6 | 0/6 | 6/6 | 4/4 |
| 2 | 8 | normal | normal | 0/6 | 0/6 | 6/6 | 4/4 |
| 3 | 24 | E;S;T;A;F;L;P | E;L;D | 5/6 | 4/6 | 6/6 | 4/4 |
| 4 | 40 | E;S;T;A;F;L;P | E;S;D;F;T;L;A | 6/6 | 6/6 | 6/6 | 4/4 |

Evaluation of the safety of a novel levamisole base/benzyl benzoate injectable, containing the equivalent of 9.1% w/v levamisole hydrochloride, in pigs.

E = Emesis; S = Salivation; T = Tremors; A = Ataxia; F = Foamy muzzle; L = Lethargy; P = Polypnea; D = Diarrhea
*Two pigs of each group are sacrificed in phase II, one hour after the administration of the corresponding drug dose.

It can be seen from Table III that no toxic symptoms are observed at the recommended dose level. Toxic symptoms at the 24 and 40 mg/kg dosages include emesis, foamy muzzle, salivation, depression, accelerated respiration, slight ataxia and slight tremors. All pigs given the exaggerated dosages return to normal within 2.5 hours. Toxic symptoms observed after the first and second treatments are similar.

EXAMPLE 4

In this example, the survivors per total, and mortality data obtained in Examples 1, 2 and 3 are combined in Table IV for comparison. The data displayed in Table IV clearly show that the levamisole base/benzyl benzoate injectable solution, containing the equivalent of 9.1% w/v levamisole hydrochloride is much safer at the 40 mg/kg body weight level than the corresponding regular and aqueous propylene glycol formulations containing the equivalent of 9.1% w/v levamisole hydrochloride.

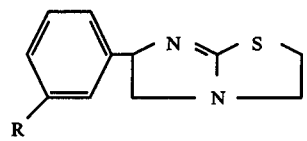

wherein R is hydrogen, amino, i-butyrylamino, trimethylacetylamino or benzoylamino and the racemic mixtures and the optical isomers thereof in benzyl benzoate.

2. A liquid composition according to claim 1 wherein R is hydrogen, amino, i-butyrylamino or benzoylamino.

3. A liquid composition according to claim 1 wherein the compounds are the 1-isomers.

4. A liquid composition according to claim 1 wherein the solution contains the compound in amounts corresponding to 5% to 20% weight by volume levamisole hydrochloride equivalent.

5. A liquid composition according to claim 1 wherein the solution contains the compound in an amount corresponding to about 9.1% weight by volume levamisole hydrochloride equivalent.

6. A liquid composition according to claim 1 wherein the compound is 1-6-phenyl-2,3,5,6-tetrahydroimidazo[2,1-b]thiazole.

7. A liquid composition according to claim 1 wherein the compound is the racemic 6-[(3-isobutyrylamino)-phenyl]-2,3,5,6-tetrahydroimidazo[2,1-b]thiazole, and the optical isomers thereof.

Table IV

Combined data from Examples 1,2 and 3 for purposes of comparison

| Dosage: mg/kg levamisole . HCl Equivalent | Survivors per Total* | | | | Percent Mortality* | | | |
|---|---|---|---|---|---|---|---|---|
| | Regular | | aq. prop. glycol 9.1% | base/benzyl benzoate, 9.1% | Regular | | aq. propyl glycol 9.1% | base/benzyl benzoate; 9.1% |
| | 9.1% | 18.2% | | | 9.1% | 18.2% | | |
| 8 | | 5/5 | | 6/6;4/4 | | 0 | | 0 |
| 16 | 10/10 | 5/5 | 10/10 | | 0 | 0 | 0 | |
| 24 | | 5/5 | | 6/6;4/4 | | 0 | | 0 |
| 32 | 2/5 | 2/5 | 5/5 | | 60 | 60 | 0 | |
| 40 | 0/5 | | 2/5 | 6/6;4/4 | 100 | | 60 | 0 |
| 48 | | 1/5 | | | | 80 | | |
| 64 | | 0/5 | | | | 100 | | |

*Formulations containing % levamisole . HCl Equivalent, as indicated

8. A liquid composition according to claim 1 wherein the compound is the racemic 6-[(3-trimethylacetylamino)phenyl]-2,3,5,6-tetrahydroimidazo[2,1-b]thiazole, and the optical isomers thereof.

9. A liquid composition according to claim 1 wherein the compound is the racemic 6-[(3-benzoylamino)-phenyl]-2,3,5,6-tetrahydroimidazo[2,1-b]thiazole, and the optical isomers thereof.

We claim:

1. A liquid anthelmintic composition for injection comprising an effective amount of a solution of a compound of formula:

10. A liquid anthelmintic composition for injection comprising a solution of 1-6-phenyl-2,3,5,6-tetrahydroimidazo[2,1-b]thiazole in amounts corresponding to 6L% to 18.2% weight by volume levamisole hydrochloride equivalent in benzyl benzoate.

11. A method for the control of helminths infecting homothermic farm and companion animals, comprising administering parenterally to the animals an anthelmintically effective amount of a liquid composition comprising a compound of formula:

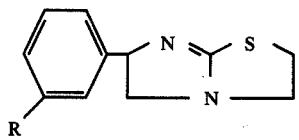

wherein R is hydrogen, amino, i-butyrylamino or benzoylamino; and the racemic mixtures and the optical isomers thereof in benzyl benzoate.

12. A method according to claim 11 wherein R is hydrogen, amino, i-butyrylamino or benzoylamino.

13. A method according to claim 11 wherein the compounds are the 1-isomers.

14. A method according to claim 11 wherein the solution contains the compound in amounts corresponding to 5% to 20% weight by volume levamisole hydrochloride equivalent.

15. A method according to claim 14 wherein the solution contains the compound in an amount corresponding to about 9.1% weight by volume levamisole hydrochloride equivalent.

16. A method according to claim 15 wherein the compound is 1-6-phenyl-2,3,5,6-tetrahydroimidazo[2,1-b]thiazole.

17. A method according to claim 15 wherein the compound is the racemic 6-[(3-isobutyrylamino)-phenyl]-2,3,5,6-tetrahydroimidazo[2,1-b]thiazole, and the optical isomers thereof.

18. A method according to claim 15 wherein the compound is the racemic 6-[(3-trimethylacetylamino)-phenyl]-2,3,5,6-tetrahydroimidazo[2,1-b]thiazole, and the optical isomers thereof.

19. A method according to claim 15 wherein the compound is the racemic 6-[(3-benzoylamino)phenyl]-2,3,5,6-tetrahydroimidazo[2,1-b]thiazole, and the optical isomers thereof.

20. A method according to claim 11, wherein the animals are swine.

* * * * *